(12) United States Patent
Rouchon et al.

(10) Patent No.: US 10,018,582 B2
(45) Date of Patent: Jul. 10, 2018

(54) PERMANENT SOIL AND SUBSOIL MEASUREMENT PROBE

(71) Applicant: IFP Energies nouvelles, Rueil-Malmaison (FR)

(72) Inventors: Virgile Rouchon, Vaucresson (FR); Bernard Langlois, St Germain en Laye (FR); Eric Ferne, Paris (FR); Claudio Fernandes-Marto, Poissy (FR); Bruno Garcia, Rueil Malmaison (FR); Corinne Loisy, Rueil Malmaison (FR); Adrian Cerepi, Pessac (FR); Olivier Le Roux, Rueil Malmaison (FR); Zsuzsanna Szabo, Rueil Malmaison (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 15/259,137

(22) Filed: Sep. 8, 2016

(65) Prior Publication Data

US 2017/0067843 A1 Mar. 9, 2017

(30) Foreign Application Priority Data

Sep. 8, 2015 (FR) .................................. 15 58326

(51) Int. Cl.
*G01N 27/12* (2006.01)
*G01N 33/00* (2006.01)
(Continued)

(52) U.S. Cl.
CPC ....... *G01N 27/125* (2013.01); *E21B 41/0064* (2013.01); *E21B 47/011* (2013.01);
(Continued)

(58) Field of Classification Search
None
See application file for complete search history.

(56) References Cited

U.S. PATENT DOCUMENTS 3,079,793 A * 3/1963 Le Bus ................... E21B 49/10
166/100
RE34,754 E * 10/1994 Dickinson ............. E21B 43/129
166/105
(Continued)

FOREIGN PATENT DOCUMENTS

CH 486 698 A 2/1970
EP 0 621 488 A1 10/1994
(Continued)

OTHER PUBLICATIONS

Noemie Taquet et al., "Efficiency of Combined FTIR and Raman Spectrometry for Online Quantification of Soil Gases: Application to the Monitoring of Carbon Dioxide Storage Sites", International Journal of Greenhouse Gas Control, vol. 12, (2013), pp. 359-371.
(Continued)

*Primary Examiner* — Jermele M Hollington
(74) *Attorney, Agent, or Firm* — Fitch, Even, Tabin & Flannery LLP

(57) ABSTRACT

A device for monitoring an formation below the ground G containing a fluid such as $CO_2$ or methane comprising a measuring cell arranged in a cavity, can an F analyzer disposed on the surface and a sealed connection connecting measuring cell to the analyzer. The measuring cell comprises two chambers that can sealingly communicate with one another. The first chamber comprises a plurality of orifices allowing passage of the fluid into first chamber, at least two inner electrodes and fluid circulator. The second chamber is impervious to the fluid. Applications include monitoring of geological storages sites for gas such as $CO_2$.

14 Claims, 7 Drawing Sheets

(51) Int. Cl.
*E21B 41/00* (2006.01)
*E21B 47/01* (2012.01)
*E21B 47/06* (2012.01)
*E21B 49/08* (2006.01)
*G01N 33/24* (2006.01)

(52) U.S. Cl.
CPC .......... *E21B 47/065* (2013.01); *E21B 49/082* (2013.01); *G01N 33/004* (2013.01); *G01N 33/0047* (2013.01); *G01N 33/24* (2013.01); *Y02C 10/14* (2013.01)

(56) References Cited

U.S. PATENT DOCUMENTS

| 5,450,012 | A | 9/1995 | Champagne et al. |
| 9,644,479 | B2* | 5/2017 | Garcia .................. E21B 49/088 |
| 2009/0091320 | A1* | 4/2009 | Flaum ...................... G01V 3/32 |
| | | | 324/303 |
| 2010/0050760 | A1* | 3/2010 | Vannuffelen ............ E21B 49/10 |
| | | | 73/152.27 |
| 2011/0181278 | A1* | 7/2011 | Chen ........................ G01V 3/32 |
| | | | 324/303 |
| 2011/0198078 | A1* | 8/2011 | Harrigan ............... E21B 49/008 |
| | | | 166/254.2 |
| 2013/0075078 | A1* | 3/2013 | Hallundbaek ......... E21B 49/082 |
| | | | 166/105 |
| 2015/0315908 | A1 | 11/2015 | Garcia et al. |

FOREIGN PATENT DOCUMENTS

| WO | 95/08129 A1 | 3/1995 |
| WO | 2014/087061 A1 | 6/2014 |

OTHER PUBLICATIONS

Thomas M. Christy, "A Permeable Membrane Sensor for the Detection of Volatile Compounds in Soil", Symposium on the Application of Geophysics to Engineering and Environment Problems, 1998, pp. 65-72.

* cited by examiner

PERMANENT SOIL AND SUBSOIL MEASUREMENT PROBE

CROSS REFERENCE TO RELATED APPLICATIONS

Reference is made to French Application No. 15/58.326, which application is incorporated herein by reference by its entirety.

BACKGROUND OF THE INVENTION

Field of the Invention

The present invention relates to monitoring the impact, on the soil and the subsoil, of anthropic activities involving or generating fluids, notably gases. More particularly, the present invention concerns the monitoring of geological storage sites for fluids such as carbon dioxide ($CO_2$) or methane.

Description of the Prior Art

Examples of such activities are waste storage (nuclear waste for example), fluid transport networks (pipelines), underground fluid storage (fuels, gas), accidental soil pollution, pollution related to non-accidental industrial activities, and geological fluid production (hydrocarbons, deep waters, geothermics).

It may be of interest to cross-reference gas exchange measurements with other types of physical measurements in order to refine, through cross-interpretation, the understanding of fluid movements in an underground formation, ideally, to guarantee the various parameters being measured and to limit environmental disturbance. These measurements need to be performed simultaneously and in the same place. Ideally, a measuring device for monitoring an underground formation containing a fluid must be able to stay in its measurement environment as long as necessary, in continuous connection or not with measurement analysis and/or a supply, optionally remote. Environmental monitoring of the impact of anthropic activities on the soil and the subsoil requires tools enabling normalized representative measurements over relatively long periods of time (years, decades).

Measuring gas exchanges in the soil and the subsoil is one aspect of environmental monitoring, which relates both to soil performance and to possible gas migration through the soil and subsoil. Within the context of measuring gas exchanges in the soil and subsoil, it may be desirable to have measuring devices accounting for a process chain ranging from signal or matter sampling through significant parameter measurement to measurement processing and uncertainty analysis. In order to ensure measurement reliability and representativity, it is desirable that the implementation of this process chain has the least possible impact on the environment to be characterized. The physical interface of a measuring device therefore is a critical element that can concentrate alone the risks of environmental disturbance and the degree of paper representation of the information.

The following documents are mentioned in the description hereafter:

Noemie Taquet, Jacques Pironon, Philippe De Donato, Hervé Lucas, Odile Barres (2013). Efficiency of Combined FTIR and Raman Spectrometry for Online Quantification of Soil Gases: Application to the monitoring of Carbon Dioxide Storage Sites. International Journal of Greenhouse Gas Control, 12, 359-371, Thomas M. Christy (1998). A Permeable Membrane Sensor for the Detection of Volatile Compounds in Soil. Symposium on the Application of Geophysics to Engineering and Environmental Problems 1998: pp. 65-72.

Document (Taquet et al., 2013) describes a device designed for collection of information relative to soil gas with collection being achieved in a (mini) wellbore. More precisely, this document describes a gas sample chamber used at the base of a well, insulated from the wellbore atmosphere by an inflatable cushion referred to as packer. The gas is extracted from the chamber by a pump and then it flows through a series of analyzers and sensors prior to being reinjected in the vicinity of the sample chamber through stainless steel tubes. Furthermore, a temperature measurement is performed at the sample chamber. Surface equipments allow measurement of the gas composition, the gas pressure and flow rate, and to maintain the packer pressure. The sample chamber is equipped with a semipermeable membrane enabling the gaseous species to be allowed into the tubes, but not liquid water. Due to the packer installation and pressure maintenance, this system is difficult to implement. Besides, there is no description of characteristics allowing ensuring that there is no disturbance of the measurement environment or the resistance to corrosion over time.

The GEOPROBE Company that develops systems dedicated to soil gas sampling is also known. These systems, made of steel, allow rapid drilling into different types of soil and recovering the gases present in the bottomhole. More particularly, the Geoprobe MIP probes (see (Christy, 1998) for example) allow driving the soil gas upwards via the circulation of a carrier gas and measuring the electrical conductivity of the soil. These probes are made of steel with measurements being performed while drilling. They are intended for specific applications and are not designed for long-term monitoring of a storage site. Furthermore, these probes require injection of a carrier gas other than the sampled gas, and they do not reinject the sampled gas, which does not guarantee that there is no disturbance of the measurement environment.

Thus, none of the devices and systems according to the prior art guarantees both that there is no disturbance of the measurement environment, measurement of the gas content, measurement of the electrical properties of soils and suitability, owing to their operation and materials, for long-term monitoring of a formation containing a fluid.

SUMMARY OF THE INVENTION

The present invention is an underground device for monitoring an underground formation containing a fluid, allowing at least sampling and analysis of the fluid present in the formation, and measurement of the electrical properties of the formation being studied. The probe according to the invention comprises a measuring cell made up of at least two chambers in which a first chamber is located where the measurements are actually performed and a second chamber protects the connections between the measuring instruments and the for analyzer of these measurements. The measurement analyzer can be remotely arranged on the surface for example, and the connection can comprise a corrosion-resistant sealed sheath.

Thus, the device according to the invention is suited for long-term monitoring of an underground formation containing a fluid, such as a geological gas storage site.

The present invention thus is a device for monitoring an underground formation containing a fluid. The device comprises at least one measuring cell arranged in a cavity provided in the underground formation, an analyzer or analyzer means for location on the surface, a connection connecting the measuring cell to the analyzer. The cell comprises at least a first chamber, a second chamber impervious to entry of the fluid, and at least three sealed inner connectors connecting the first chamber to the second chamber with the connection means or a connector providing a sealed connection of the measuring cell to the analyzer, and the connection providing sealed protection wherein, the first chamber comprises:

a plurality of orifices allowing passage of the fluid into the first chamber, at least two inner electrodes electrically connected with at least two of the inner connectors, with the inner electrodes being connected to the analyzer through the connector and the connector cooperating with the inner connectors, fluid circulation means or a fluid circulator are connected to the analyzer while being electrically connected with at least one of the connectors and with the connection.

According to one embodiment of the invention, the device can additionally comprise at least two outer electrodes, two inner connectors connecting the two chambers, two sealed outer connectors located on at least one wall of the first chamber, the wall being in contact with the formation, the outer electrodes cooperating with the outer connectors, the outer electrodes being connected to the analyzer through the connector, the connector cooperating with the two inner connectors and the two outer connectors.

According to an embodiment of the invention, the connector can comprise a power supply supplying the electrodes, and the sealed protection can comprise a sealed sheath protecting at least the circulator and the power supply.

Advantageously, the first chamber can be filled with a permeable porous material having known petrophysical and electrical properties.

Preferably, the petrophysical properties can be at least porosity and permeability, and the electrical properties can be at least electrical conductivity.

According to an embodiment of the invention, the connection, the chambers and the connectors can be made of PTFE.

According to an embodiment of the invention, the analyzer can at least comprise at least one of a fluid analyzer and a resistance measuring meter.

According to an embodiment of the invention, the fluid circulation can comprise at least a pipe, a fluid suction system and a fluid reflux system.

Advantageously, the fluid circulation can comprise at least two pipes, a fluid suction system and a fluid reflux system.

Furthermore, the invention relates to a use of the device according to the invention for monitoring a geological storage site for a gas such as $CO_2$ or methane.

Preferably, a calibration stage can be carried out prior to injecting gas into the geological storage site when using the device according to the invention for monitoring a geological gas storage site.

Moreover, the invention relates to a method for monitoring an underground formation containing a fluid, wherein at least one device for monitoring an underground formation containing a fluid according to the invention is used and wherein at least the following stages are carried out:

drilling a cavity for receiving the measuring cell of the device;

connecting the measuring cell to the connection of the device, arranging the measuring cell within the formed cavity and arranging the analyzer on the surface, connecting the analyzer to the connector of the device, performing measurements using the measuring cell and analyzing the measurements using the analyzer.

BRIEF DESCRIPTION OF THE FIGURES

Other features and advantages of the method according to the invention will be clear from reading the description hereafter of embodiments given by way of non-limitative example, with reference to the accompanying figures wherein.

DETAILED DESCRIPTION OF THE INVENTION

The invention concerns a device for monitoring an underground formation containing a fluid. The fluid can be gas, such as $CO_2$ or methane, or a liquid such as a liquid hydrocarbon phase. The fluid F may have been, not restrictively, intentionally stored in the formation being studied (for example in the case of geological $CO_2$ storage) or it can result from a degradation of products stored in the formation being studied (for example in the case of geological waste storage), or it can be a natural fluid geologically trapped in a subsoil formation.

The device according to the invention comprises a measuring cell to be arranged in a cavity C provided below ground level G in the underground formation being considered. The cavity C may be formed by drilling, for example, to the size of the measuring cell MA so that the cell is in direct contact with the formation. According to the invention, the measuring cell has at least a first chamber and a second chamber. The measurements are actually performed in the first chamber using measuring instruments, and the second chamber serves as a protection for connection connecting the measuring instruments to an analyzer of these measurements. The analyzer can be arranged for example on the surface of the ground G. According to the invention, the connection provides a sealed connection between the measuring cell and the analyzer and the connection provides sealed protection.

Furthermore, at least three inner connectors provides a sealed connection of the first chamber to the second chamber which passages of the measurements.

Moreover, the first chamber comprises at least:

a plurality of orifices allowing passage of the fluid F into the first chamber;

at least two inner electrodes electrically connected with at least two of the inner connectors, the inner electrodes are electrically connected to the analyzer through the connection which is electrically connected with the inner connectors. The electrodes perform electrical measurements relative to the fluid present in the first chamber;

a fluid circulator is electrically connected to the analyzer and to at least one of the connectors which is electrically connected with connections.

Figure 1:
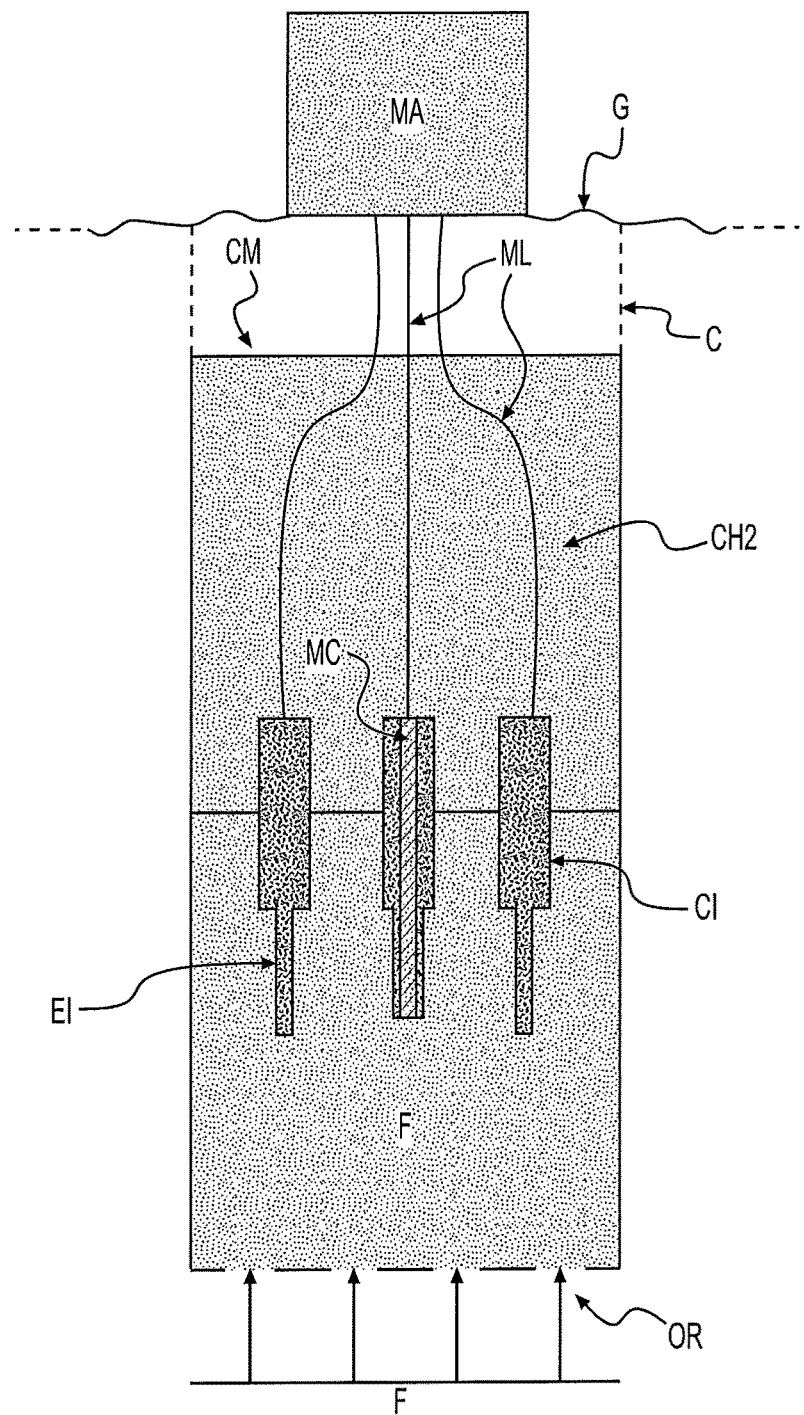
FIGS. 1 to 5 diagrammatically illustrate in cross-sectional view of different embodiments of the device for monitoring an underground formation containing a fluid according to the invention.

FIG. 1 shows a non-limiting embodiment of the device according to the invention. The various elements of the device according to the invention can be arranged differently in relation to one another and in the absolute. FIGS. 2 to 5 show, by way of non-limitative and non-exhaustive examples, other variant embodiments of the device according to the invention. FIGS. 1 to 5 correspond to a section along a vertical plane of the device for monitoring an underground formation containing a fluid.

The device according to the invention comprises a measuring cell CM which is placed in a cavity in the underground formation which is being considered. The cavity may have been formed by drilling for example, to the size of measuring cell CM, so that cell CM is in direct contact with the formation. According to the invention, measuring cell CM has at least a first chamber CH1 and a second chamber CH2. Advantageously, the second chamber CH2 is positioned above the first chamber CH1 as shown by way of non-limitative example in FIG. 1.

According to the invention, the device is equipped with analyzer MA that can be remotely arranged on the surface of the ground G for example. The connections ML provide a sealed connection between the measuring cell CM and the analyzer MA which is shown as resting on the ground G. According to the invention, the connections ML are themselves protected by seals.

According to the invention, the wall of first chamber CH1 is pierced with a plurality of orifices OR in the bottom which are used for sampling of fluid F present from the formation that has passed through the orifices into the interior CHI within the inner volume of first chamber CH1. According to the invention, the second chamber CH2 is impervious to the fluid. Moreover, according to the invention, at least three inner connectors CI provide a sealed electrical connection of first chamber CH1 to second chamber CH2.

According to the invention, the first chamber CH1 additionally comprises at least two inner electrodes EI electrically connected with at least two of the inner connectors CI of the cell. The inner electrodes EI are also connected to analyzer MA through connections ML which are electrically connected with inner connectors CI.

According to the invention, first chamber CH1 also comprises circulator MC for the fluid F collected in first chamber CH1. The circulator MC for the fluid F collected in first chamber CH1 is electrically connected to the analyzer MA while being electrically connected with at least one of the connectors CI and with the connection ML.

According to the invention, the connections provide a sealed electrical connection between the measuring cell and the analyzer which enables electrical transmission without loss of the measurements performed by the measuring cell to the analyzer. Furthermore, the connections are protected by seals. This guarantees that the electrical connections will not degrade over time, and thus contributes to the durability and the suitability of the device according to the invention for the long-term monitoring of an underground formation containing a fluid.

The imperviousness of the interior of the second chamber CH2 allows protection of the parts of the device according to the invention which are positioned in the second chamber (at least connection ML as shown in FIG. 1), and thus enhances durability of elements inside the second chamber, and therefore to the suitability of the device according to the invention to provide long-term monitoring of an underground formation containing a fluid.

The imperviousness of the inner connectors is intended to prevent passage of part of the fluid collected in the first chamber into the second chamber to prevent erroneous data transmission to the analyzer of the amount of fluid that is collected and to preserve the integrity of the second chamber CH2 and of the part of the measuring elements of the device according to the invention (at least connection ML as shown in FIG. 1) that it contains.

Figure 2:
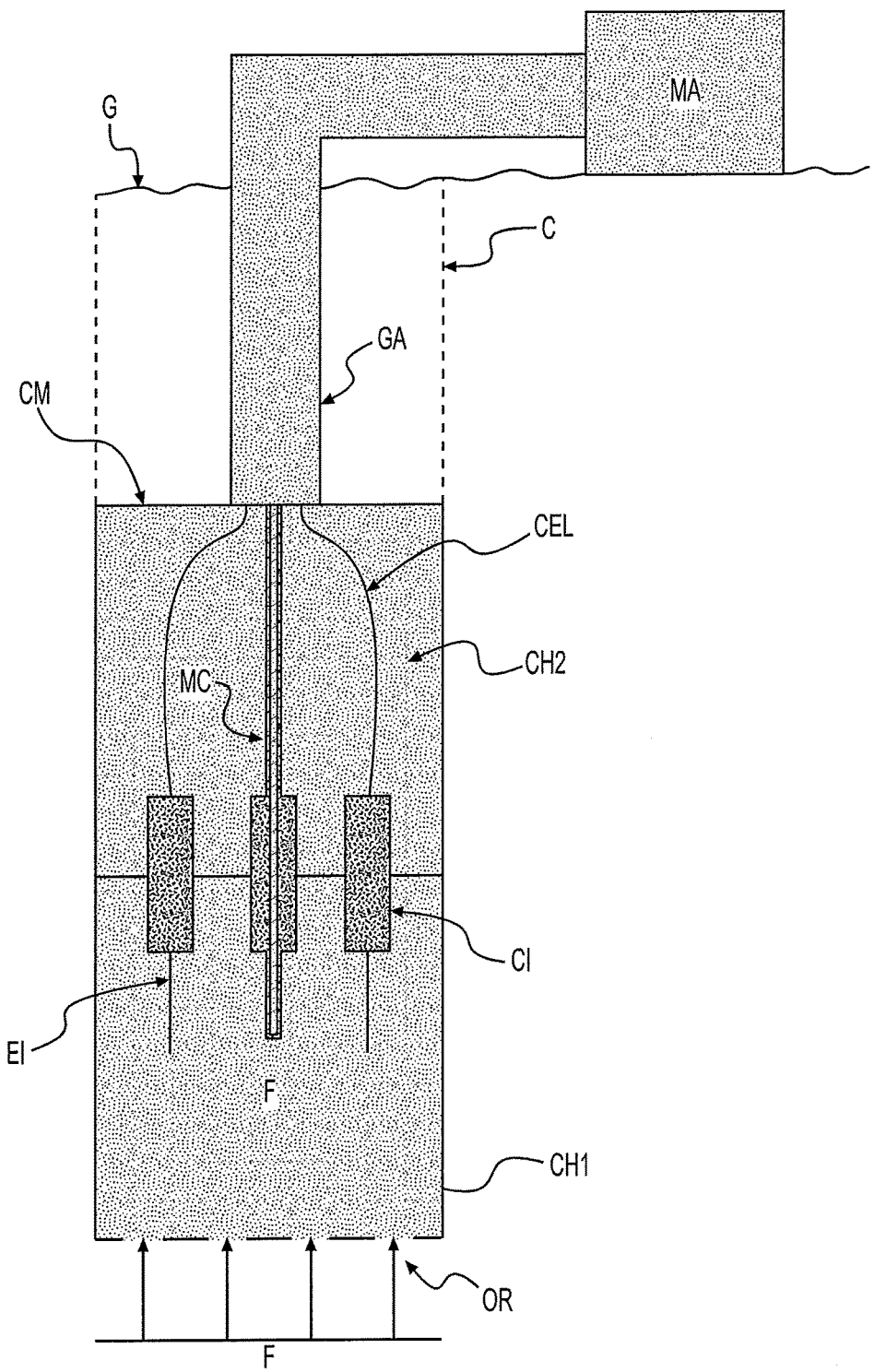

According to an embodiment of the invention, the connections comprise a power supply for the electrodes, and the sealed protection comprises a sealed sheath protecting at least the fluid circulator and the power supply. FIG. 2 shows by way of non-limitative example a variant of this embodiment. For this variant, the sealed protection comprises a sealed sheath GA connecting the top of measuring cell CM which is below ground level G to analyzer MA, and the power supply corresponds to electrical cables CEL cooperating with inner connectors CI cooperating with two inner electrodes EI. According to this embodiment, a first part of electrical cables CEL runs through second chamber CH2 and a second part (not shown), inserted in sheath GA, connects the top of the second chamber to analyzer MA. According to this embodiment of the invention, an opening is provided in the top of second chamber CH2 which cooperates with sheath GA. According to this embodiment of the invention shown in FIG. 2, the fluid F taken from first chamber CH1 of measuring cell CM is taken up by fluid circulator MC in which a first part thereof is located in first chamber CH1, a second part runs through at least one of the inner connectors CI, a third part runs through second chamber CH2 and a fourth part (not shown) which is inserted in sheath GA, connects the top of second chamber CH2 to the analyzer MA. According to an embodiment of the invention, the electrical cables are insulated with a silicone sheath and the sheath is made of polymer with a helical steel armor.

FIGS. 3-7, illustrate other embodiments of the present invention which show hereafter by way of non-limitative and non-exhaustive example connections comprising a sheath GA, electrical cables CEL and remote analyzer MA. The part of the electrical cables and the part of circulator MC arranged outside measuring cell CM are inserted in sheath GA. Any other layout and configuration of the connections allowing measuring cell CM to be connected to analyzer MA is however possible, and the analyzer MA can be proximate or remote.

According to an embodiment of the present invention, the orifices of the first chamber can be:

(1) covered with a semi-permeable/hydrophobic membrane (of 0.2 μm-diameter hydrophobic polypropylene type for example) to prevent water sampling in the first chamber CH1 and water upflow in the fluid circulator MC towards the analyzer MA. This embodiment is particularly suited when the fluid of interest is a gas and in the case of an area where submergence is considered (flood-risk area, high water table fluctuations, heavy rains and bad drainage conditions), or (2) covered with a geotextile with geotextiles having the property of being hydrophilic (which ensures good hydric and electrical coupling between the inner volume of the first chamber and the formation) and anti-particulate (thus preventing fine particles from entering the inner volume of the first chamber). This embodiment can be preferably used in well drained areas, far from waterways, out of the reach of the water table and submergence risk free, or (3) free, that is not covered with any material. This embodiment allows maximum connectivity of the inner volume of the first chamber with the outside medium, and thus to measure fast gas composition fluctuations.

According to a particular embodiment of the present invention, the first chamber and the second chamber are made of polytetrafluoroethylene (PTFE) to ensure a good durability for measuring cell CM and a minimum chemical effect by the close environment.

Figure 3:
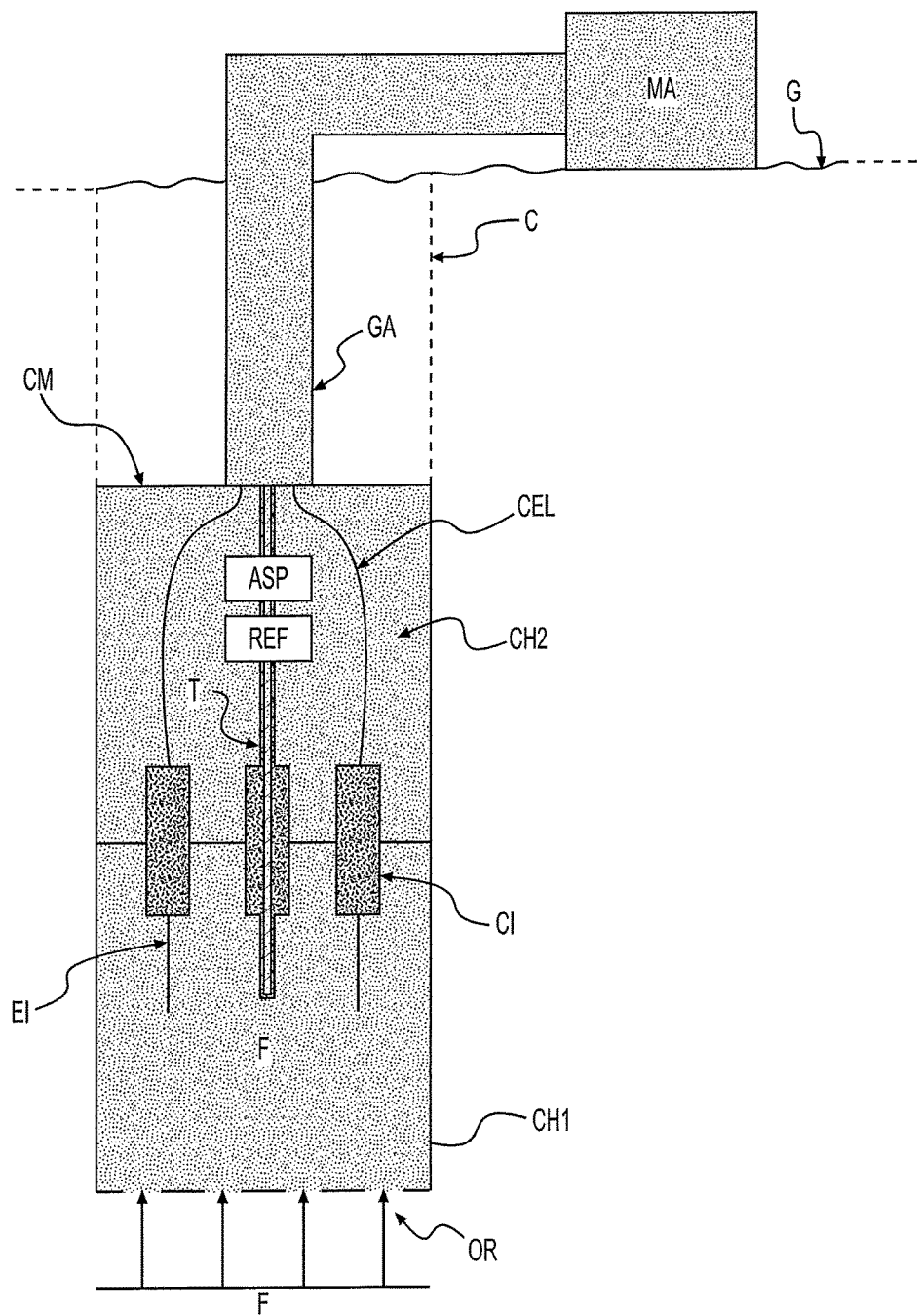

According to a non: limitative embodiment of the present invention shown in FIG. 3, the fluid circulator MC comprises at least a tube T, a suction system ASP and a reflux system REF. Suction system ASP allows the fluid sampled in first chamber CH1 to be sucked into at least one inner connector CI, then into tube T, and to be transferred to analyzer MA. Reflux system REF allows the fluid F, once collected and analyzed by analyzer MA, to be refluxed to the formation by passing again through the tube T, the inner connector CI, the first chamber CH1, then the orifices OR of first chamber CH1. By sampling the fluid and reinjecting the sampled fluid into the formation, this embodiment allows significant limitation of measurement environment disturbance, which is suitable for long-term monitoring of a site containing a fluid. Preferably for example, suction system ASP and reflux system REF are remote systems arranged on the formation surface. The embodiment of the invention shown in FIG. 3 comprises a connection including a sheath GA, electric cables CEL and remote analyzer MA. The part of electric cables CEL and the part of tube T outside measuring cell CM is inserted in sheath GA. Any other layout and configuration of the connections and any other method of cooperation of these connections with the fluid circulation are however possible, and the analyzer can furthermore be remote or not.

Figure 4:
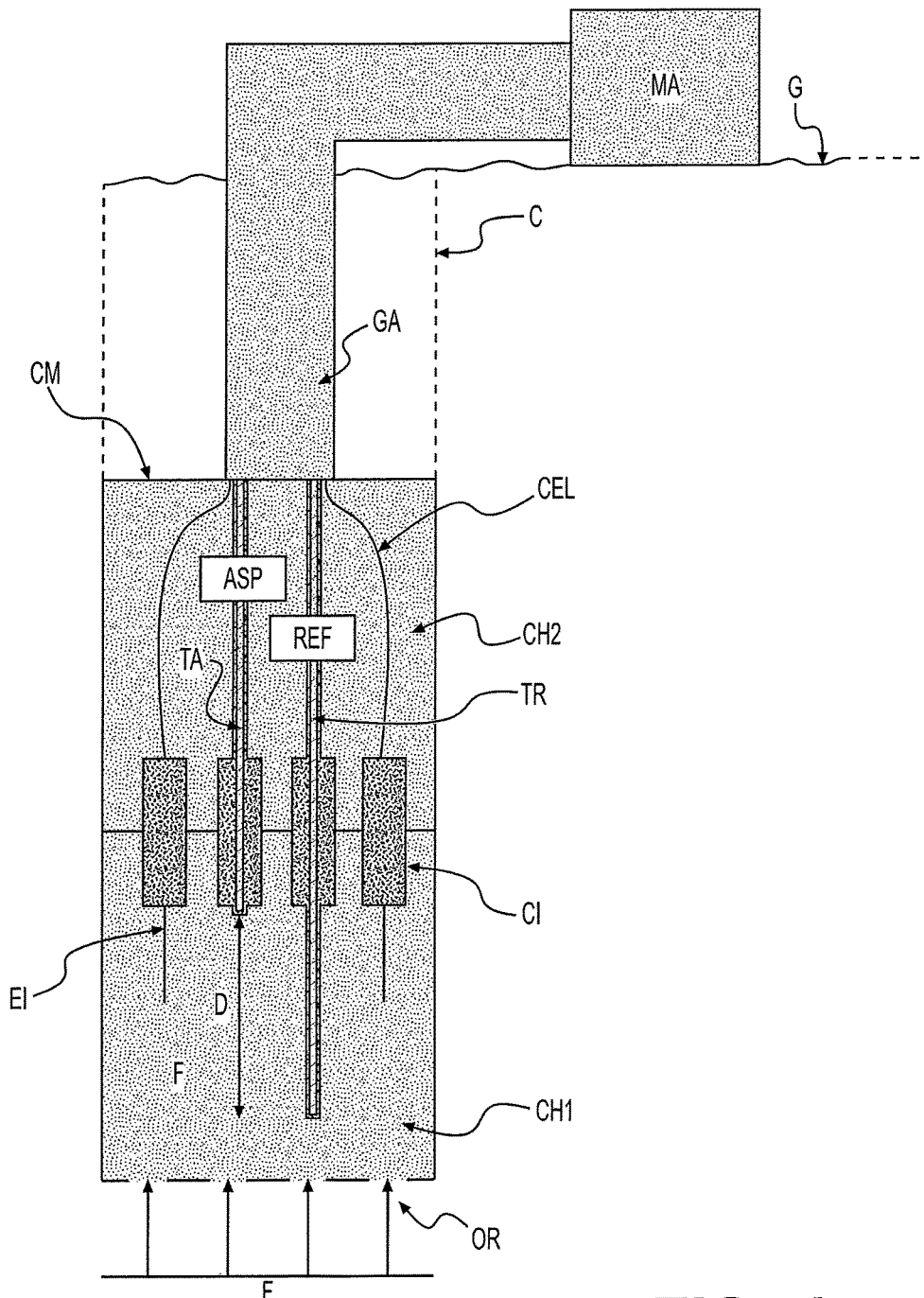

According to a non-limitative embodiment of the invention shown in FIG. 4, the fluid circulation comprises two tubes TA and TR with tube TA being connected to suction system ASP and tube TR being connected to reflux system REF. Preferably, tube TR penetrates deep into the inner volume of first chamber CH1, while the termination of tube TA in first chamber CH1 substantially corresponds to the base of connector CI with which it cooperates. This configuration allows maximizing the distance D between the suction point and the reflux point, and thus maximizing stirring of the gas between the two tubes. Thus, the gas composition variations in the cell are more finely detectable. Preferably, distance D corresponds to 70% of the height of first chamber CH1. The embodiment of the invention shown in FIG. 4 comprises connections including a sheath GA, electrical cables CEL, remote analyzer MA. The part of electrical cables CEL and the parts of tubes TA and TR outside measuring cell CM are inserted in sheath GA. Any other layout and configuration of the connections and any other method of cooperation of these connections with the fluid circulation are however possible, and the analyzer can furthermore be remote or not.

According to an embodiment of the invention, the analyzer MA comprises at least one fluid analyzer, which can be a remote analyzer arranged on the surface G or not. The fluid analyzer allows detection and quantification (concentration assessment for example) of at least one type of fluid. Preferably, the fluid analyzer allows at least detection and quantification of the fluid injected into the formation.

According to an embodiment of the invention, the inner electrodes can be used for electrical resistivity (resistance) measurements in the medium. According to this embodiment, at least part of the inner volume of the first chamber is advantageously filled with a porous reference material (preferably permeable to the fluid F collected through the orifices) so that at least part of inner electrodes EI is in contact with this porous material. A porous reference material is understood to be a material whose petrophysical and electrical properties are known. Preferably, the petrophysical properties of the porous reference medium are at least porosity and permeability. Preferably, the electrical properties of the porous reference medium are at least the electrical conductivity. Advantageously, the porous material can be quartz sand. Thus, the fluid collected in the first chamber can lodge itself in the pores of the porous material, and a resistivity measurement, through the inner electrodes, in contact with this at least partly fluid-saturated material, is performed.

More preferably, the analyzer comprises at least one resistivity meter, remote and arranged on the surface G or not. The connections can then include electrical cables allowing connection of the inner connectors cooperating with the electrodes internal to the resistivity meter.

Figure 5:
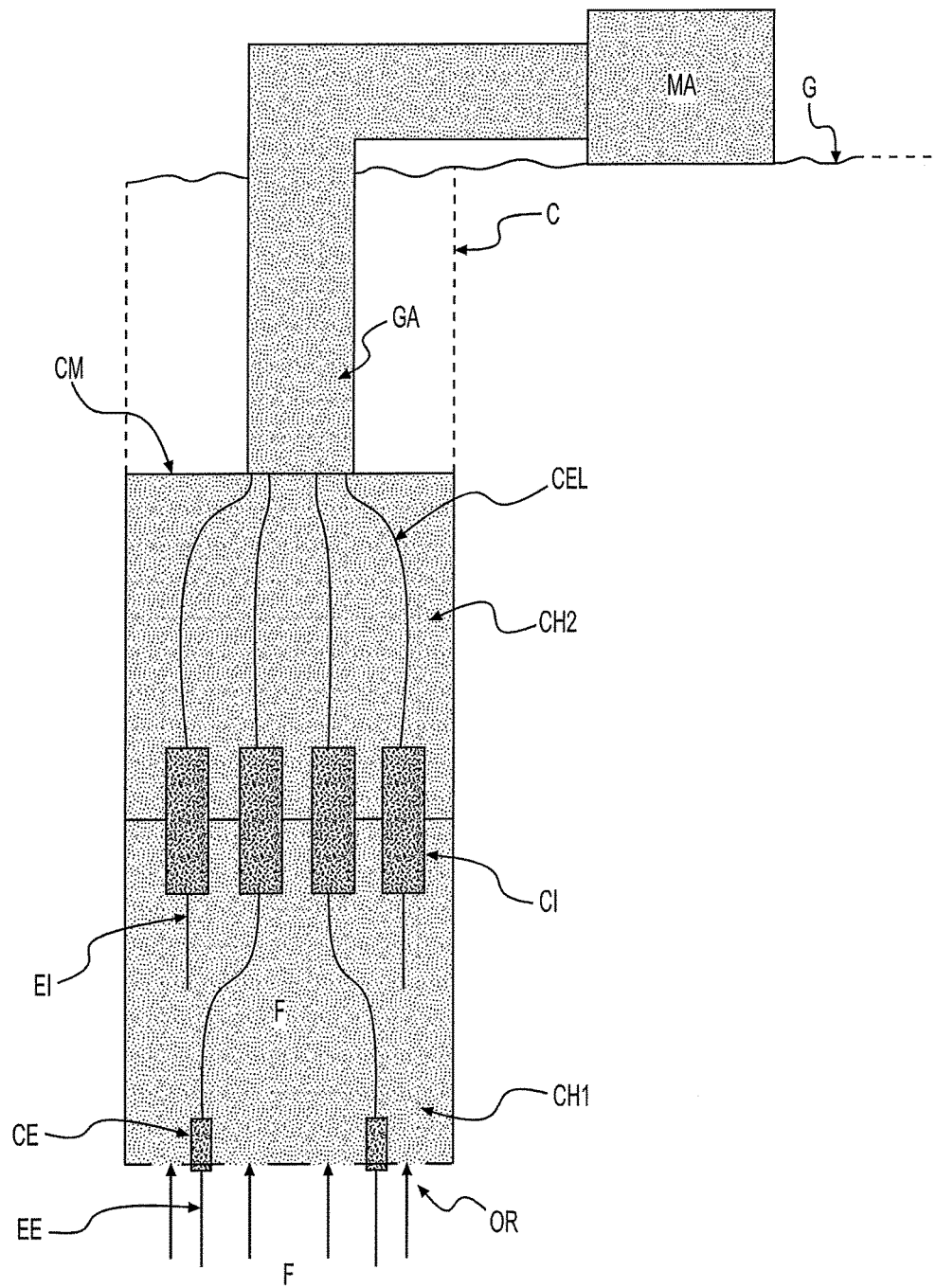

According to a non-limitative embodiment of the invention illustrated in FIG. 5 (the fluid circulators are not shown in this figure for simplification reasons), at least two sealed outer connectors CE are positioned on one of the walls of first chamber CH1 in contact with the outside of measuring cell CM with outer connectors CE cooperating with at least two outer electrodes EE. Furthermore, according to this embodiment, the device also comprises at least two additional inner connectors CI. The additional inner connectors CI allow passage of connections (such as electric cables CEL shown in FIG. 5) between the outer connectors CE and the analyzer MA. Advantageously, the wall on which outer connectors CE are arranged is in contact with the formation of interest. Thus, outer electrodes EE which run through this wall via outer connectors CE allow electrical measurements to be performed within the formation being studied. Advantageously, analyzer MA comprises at least one resistivity meter and the electrical measurements performed by outer electrodes EE concern an electrical resistivity measurement in the formation of interest. According to a particular embodiment of the present invention, electrical resistivity measurements are performed using the at least two inner electrodes EI and the at least two outer electrodes EE positioned as described above. Thus, inner electrodes EI allow calibration of the resistivity measurement on a known simple porous medium (such as quartz sand) and therefore to serve as a reference in relation to the resistivity measurements performed with outer electrodes EE that are subject to more unknowns regarding the porous medium where they are inserted (mineralogical composition, porosity, grain size). Notably, this embodiment can be useful for quantifying and monitoring a potential resistivity measurement drift related to a property alteration of the inner and/or outer electrodes. The embodiment of the invention illustrated in FIG. 5 comprises connections including a sheath GA, electrical cables CEL and remote analyzer MA. The part of the electrical cables CEL outside measuring cell CM is inserted in sheath GA. Any other layout and configuration of the connections and any other cooperation of these connections with fluid circulation means are possible, and the analyzer can furthermore be proximate or remote. According to another embodiment of the invention, at least one of the inner electrodes and the outer electrodes are used for performing time domain reflectometry (TDR) measurements. According to this embodiment, the analyzer MA comprise a time domain reflectometer and the inner and/or outer electrodes are connected through connections (preferably electrical cables) to the time domain reflectometer. This an embodiment allows quantifying the dielectric constant of the formation under study to be proportional to the water saturation of the formation being studied.

According to an embodiment of the present invention, the device furthermore comprises a temperature probe communicating with the inner volume of the first chamber through an inner connector. Thus, the device also allows measuring the temperature within the formation being studied. This temperature measurement can be useful for determining thermal conductivities in the formation being studied, by comparison with a surface temperature measurement, and for correcting the electrical resistivity measurements performed by at least one of the inner and outer electrodes biased by the effects of temperature on the medium conductivity.

According to an embodiment of the present invention, the device according to the invention also comprises a soil moisture measuring device. Such measurements can indeed allow calibration of the electrical measurements performed by the inner and outer electrodes regarding the soil moisture rate variations.

Variants

Variants of the present invention comprising elements enabling automated measurements over time are presented hereafter. The variants described below can be combined, alone or in combination, with any one of the embodiments described above.

According to an embodiment of the present invention, the device furthermore includes automaton allowing preprogramming of the measurements to be performed, whether of an electrical, a geochemical or a temperature type. The automaton can for example allow defining a geochemical measurement sequencing by triggering successively with time, according to a given periodicity, sampling of the fluid, as well as transfer and analysis of this fluid. Likewise, the automaton can allow triggering electrical measurements with a certain periodicity, according to some parameters (number of electrodes involved in the measurement, electric current supplied, etc.).

According to an embodiment of the present invention, the device also comprises a data collector (such as the DT85GLM model marketed by the DIMELCO Company for example) and data transmission. The data collector allows collection of the measurements analyzed in the analyzer and to transmit them in real time by the data transmission.

According to an embodiment of the present invention, the collected data transmission provide remote transmission (modem enabling internet connection for example). Preferably, the transmission of the data collected by the collector is a 3G modem.

Thus, the device according to the invention allows the data collected on the site to be transmitted automatically and in real time to personnel who are able to make ad hoc decisions in case of abnormal measurements performed in situ by the device.

According to an embodiment of the present invention, the data collector allows alert trigger points to be taken into account and it is able to trigger an alert. Thus, if an amount of fluid above a given set threshold is detected through the fluid analyzer, the data collector is able to send an alert, for example to specialists or to the authorities, through an email message, an audible warning, etc.

According to an embodiment of the present invention, the power supply of the device according to the invention is provided by a solar panel which is connected to a battery.

According to another embodiment of the present invention, at least the analyzer, the data collector and possibly automaton are protected on the surface in a sealed shelter.

According to an embodiment wherein the device of the invention utilized automaton, a data collector and a remote transmission for collected data, the invention allows performing measurements in an automatic and preprogrammed manner, to analyze measurements by using the analyzer, to collect the results of these measurements through the collector, then to transmit them to a potentially distant specialist remote transmission. A device comprising such elements is suited for long-term permanent monitoring of a site containing a fluid whose (chemical and/or spatial) evolution needs to be monitored.

Use of the Invention

The invention also concerns the use of the device according to the invention for monitoring an underground formation containing a fluid.

The invention particularly concerns the use of the device according to the invention for monitoring a geological storage site for a gas such as carbon dioxide ($CO_2$) or methane.

Preferably, using the device according to the invention for monitoring an underground formation containing a fluid requires a device calibration stage prior to the monitoring phase. In order to guarantee characterization of the impact on the environment of the soil and subsoil of a geological storage site, characterization prior to the industrial activity in question needs to be done in order to define the reference state of the environment (also referred to as base line). The environmental monitoring tools must therefore provide for characterization of the natural environment, the spatial heterogeneities and the temporal variability thereof. It must also be possible to subsequently use the monitoring tools to measure the impact of an activity on the basis of a previously defined reference state.

Once installed on site, the device according to the invention can be used in continuous and/or permanent acquisition mode, or for chronic measurements. In the case of permanent measurement, the analyzer MA can be connected to measuring cell CM by permanent connections. In the case of chronic measurement, the connections can be removed and must allow the analyzer MA to be temporarily disengaged from measuring cell CM, to enable protection of the analyzer MA between two measurements.

Moreover, the invention concerns a method of monitoring an underground formation containing a fluid by a device for monitoring an underground formation containing a fluid according to any one of the variants described above, and comprising at least the following stages:

drilling a cavity C below the ground G for receiving the measuring cell of the device, connecting the measuring cell to the connections of the device, arranging the measuring cell within the cavity and arranging the analyzer of the device on the surface, connecting the analyzer to the connections of the device, performing measurements using the measuring cell and analyzing the measurements using the analyzer.

Application Example

The features and advantages of the method according to the invention will be clear from reading the application example hereafter.

Figure 6A:
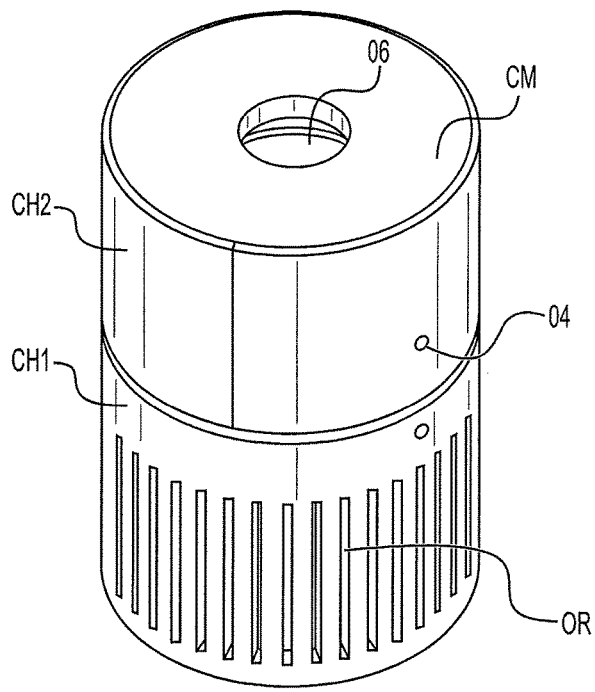
FIG. 6A illustrates an external view of an embodiment of the measuring cell of the device for monitoring an underground formation containing a fluid according to the invention, and FIG. 6B corresponds to a vertical section along the measuring cell of the device according to the invention as shown in FIG. 6A, FIGS. 7A and 7B respectively show the evolution of the electrical resistivity measured by inner electrodes and outer electrodes as a function of the water saturation, for three different assembly configurations of the measuring cell of the device according to the invention.
Figure 6B:
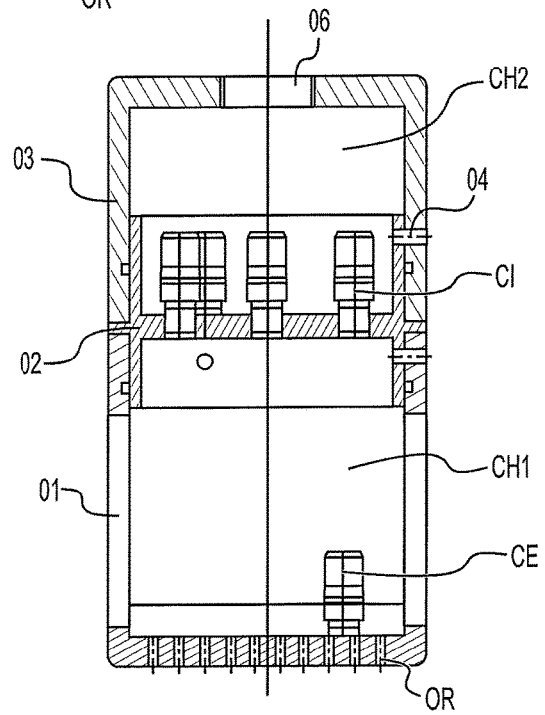

The application example in question relates to the monitoring of an underground formation into which $CO_2$ has been injected, monitoring being achieved according to a particular variant of the device of the invention illustrated in FIGS. 6A and 6B. More precisely, FIG. 6A shows an external view of measuring cell CM according to the embodiment of the invention in question, and FIG. 6B shows a vertical section along the measuring cell CM according to the same embodiment. As FIG. 6B corresponds to a section in the volume of measuring cell CM. All of the elements making up the embodiment in question are not shown.

Thus, the device as implemented for this application of the device according to the invention is characterized by:

- a measuring cell CM made up of a first semi-open body 01, of cylindrical revolution, the opening of the first body being oriented upwards, the first body being provided with a cover 02 to form a closed first chamber CH1, cover 02 being surmounted by a second semi-open body 03, of cylindrical revolution, the opening of the second body being oriented downwards, so as to form, with the cover 02, a closed second chamber CH2. Thus, according to this implementation example, cover 02 forms both the upper wall of first chamber CH1 and the lower wall of second chamber CH2 of the cell. According to this example, first body 01, cover 02 and second body 03 tightly fit into one another through the agency of silicone doughnut rings, and they are secured by stainless steel pins 04 press-fitted in orifices provided for that purpose. According to the same implementation mode, the vertical wall of the first chamber is pierced with oblong orifices OR and the basal wall is pierced with circular orifices OR to allow passage of the gas present in the formation of interest into the inner volume of first chamber CH1. The top of second chamber CH2 comprises an opening 06 allowing at least passage of connection means ML. Still according to this example, the two bodies and the cover are made of PTFE to provide the durability of measuring cell CM. The chambers are approximately 100 mm in diameter and 100 mm high each,
- five orifices pierce cover 02 of measuring cell CM with cover 02 corresponding both to the upper wall of first chamber CH1 and to the lower wall of second chamber CH2, to allow communication between the two chambers through inner connectors CI,
- two orifices pierce the lower wall of first chamber CH1 to allow passage of outer electrodes EE through outer connectors CE;
- an inner volume of first chamber CH1 is 90% filled with quartz sand of grain size 300 µm. This filling allows having a 2 cm-high gas overhead at the top of the inner volume of first chamber CH1;
- outer walls of measuring cell CM (including the orifices that pierce the walls of first chamber CH1) covered with a geotextile glued with a silicone-based glue. In addition to providing good hydric and electrical coupling between the inside of first chamber CH1 and the formation, and prevent passage of particles into the inner volume of first chamber CH1 with the use of geotextile allowing keeping the quartz sand within first chamber CH;
- four electrodes (not shown) made of tungsten guarantee good electrical conductivity and excellent corrosion resistance. More particularly, the electrodes are crimped on adapters made up, on one side, of a ⅛" fitting of Swagelok® double ring type and, on the other side, of a ⅛" male NPT type fitting. Two of them (referred to as inner electrodes) are screwed in two of the tapped Teflon® orifices allowing communication between the first CH1 and the second CH2 chamber. The other two electrodes (referred to as outer electrodes) are screwed in the two orifices allowing communication of first chamber CH1 with the formation being studied. An inner connector CI or an outer connector CE according to the invention is thus made up of a ⅛" fitting of Swagelok® double ring type and a ⅛" male NPT type fitting. The inner CI and outer CE connectors associated with inner electrodes and outer electrodes respectively comprise electrical tin connectors allowing connection (through crimping) of the electrodes to the electric cables cooperating with the connectors CI, CE respectively. At least the part of the electrical cables located in first chamber CH1 and the electrical connectors of outer connectors CE are electrically insulated from the inner volume of first chamber CH1 by a heat-shrink sheath. The electrical cables associated with the outer electrodes rise towards the analyzer by passing through second chamber CH2 via two of the orifices pierced in the cover of measuring cell CM, the passage being sealed by a silicone-based glue,
- fluid circulation (not shown) comprising a fluid suction and a fluid reflux, with each one comprising two tubes, aspiration and reflux tubes respectively. The tubes of the fluid circulation are standard stainless steel thin-rim ⅛" tubes (1 mm (0.04") inside diameter). They are crimped on inner connectors CI made up, on one side, of a ⅛" fitting of Swagelok® double ring type and, on the other side, of a ⅛" male NPT type fitting, then directly screwed in the tapped Teflon® orifices allowing communication between the two chambers. The suction tube ends at the top of first chamber CH1. The reflux tube runs through the cover and first chamber CH1, up to one centimeter above the basal wall of chamber CH1,
- a temperature probe (not shown) of PT100 type (marketed by the Prosensor Company), crimped through an inner connector CI made up, on one side, of a ⅛" fitting of Swagelok® double ring type and, on the other side, of a ⅛" male NPT type fitting, directly screwed in the tapped Teflon® orifices allowing communication between the two chambers. This temperature probe is a feed-through probe that runs halfway down first chamber CH1. It is supplied by an electric cable,
- connections (not shown) comprising a protection sheath, armored and flexible, connected to the top of second chamber CH2 by two nuts on either side. The sheath rotates freely about its principal axis, at the connection with the top of second chamber CH2, so as to limit stresses thereon. The four electrical cables of the electrodes, the electric run through opening 06 provided in the top of second chamber CH2 and the sheath prior to joining the remote analyzer. The sheath is five meters long. The electrical cables and the tubes are six meters long, allow direct connection with the remote analyzer at the surface, remote analyzer comprising a resistivity meter of Syscal Junior 24 (Iris Instruments®) type and a gas analyzer allowing to detect and to quantify $CO_2$, such as the LI-820 detector marketed by the LI-COR Company for example.

The device according to the invention as described above was installed in a cavity provided by drilling in the formation being studied.

100-mm holes were drilled with an auger bit and the soil samples were carefully collected for each 10-cm depth interval. Three holes were drilled at depths of: (1) 180 cm (2) 120 cm (3) 60 cm. The soil samples were analyzed in the laboratory to define their proportion of total organic carbon, mineral carbon, the major minerals distribution (clays, tectosilicates and carbonates), the porosity and the grain size distribution.

A fraction of the soil corresponding to the base of the hole is coarsely screened in order to remove the stones and the roots. This screened soil is placed in the bottom of the hole intended to receive the device according to the invention in order to fill again the remaining last 20 centimeters. Measuring cell CM is manually lowered by pushing it through armoured sheath GA and by guiding the verticality of measuring cell CM using a pole. Once contact is made with the base of the hole, measuring cell CM is driven in using the pole while ensuring that outer electrodes EE penetrate in the base of the hole by controlling the insertion distance. Once measuring cell CM in place, the hole is filled in with sand (100-µm diameter) until the cell is covered therewith, so as to guarantee good mechanical coupling of the porous media between the inside of measuring cell CM and the formation studied. The hole is then flooded with fresh water in order to rework the porous medium, to fill in any space left unfilled and to maximize the hydric coupling between measuring cell CM and the formation studied. The hole is finally filled in with the sampled soil while respecting the vertical zonation thereof. The terminations of tubes TA, TR and of cables CEL are then connected to the analyzer MA arranged on the installation surface.

Figure 7B:
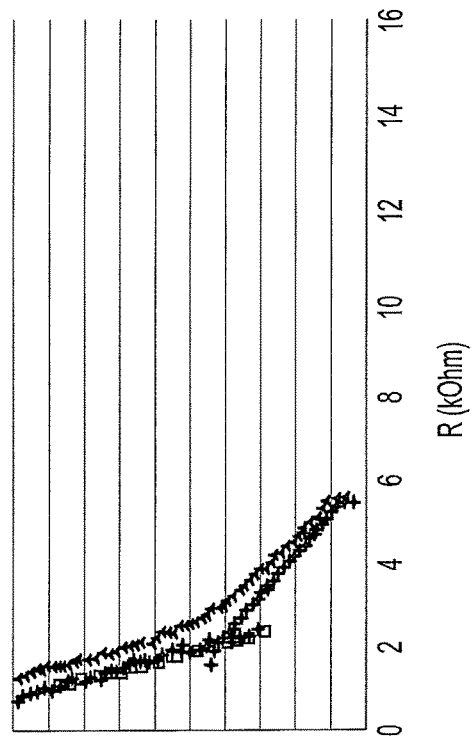
Figure 7A:
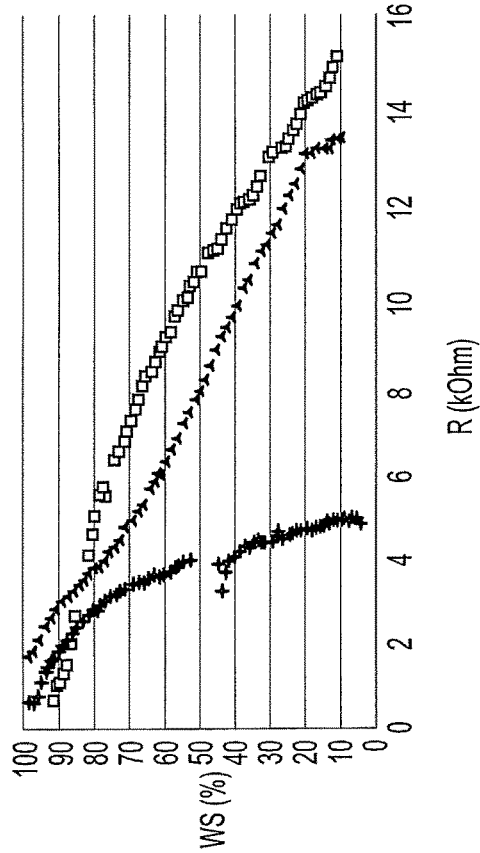

A stage of calibrating the device according to the invention has been carried out prior to the monitoring phase proper. More precisely:

electrical resistivity measurements are performed by a drainage test by saturating the hole intended to receive measuring cell CM with fresh water and by measuring the evolution of the resistivities upon drainage thereof through natural drainage and evapotranspiration. Measurements comparable to those acquired in the laboratory must be obtained. FIGS. 7A and 7B respectively show examples of calibration curves for resistivity R measured by inner electrodes EI and outer electrodes EE as a function of the water saturation SW for three different assembly configurations of measuring cell CM, temperature measurements using the temperature probe are checked by comparison with temperatures recorded at the surface of the device installation according to the invention, validation of the fluid circulation is carried out by injecting a reference gas into reflux tube TR until a measurement of the reference composition thereof in suction tube TA is obtained. Injection is then stopped and the fluid circulation is restarted in a closed loop. The measured exchange rates must correspond to those measured in the laboratory for equivalent water saturations (indicated by the resistivities).

The measurements performed by the invention installed in the formation and calibrated are resistivity measurements, temperature measurements and gas analyses. The system is permanently installed and measurements are performed every minute upon gas injection, and every 30 minutes after the injection.

Such a device, made up of fluid-proof elements and comprising fluid circulation allows the fluid collected in the formation to be refluxed, is suited for long-term monitoring of a formation and, moreover, without measurement perturbation. The ability to perform, in a single measuring cell, different types of physical measurements (electrical, geochemical, temperature) avoids multiple installations on the site and thus allows reduction of installation costs and measurement environment disturbance. Moreover, measurements of various types, performed simultaneously and at a single measuring point, enable more reliable cross-interpretation of the different physical measurement types.

The invention claimed is:

1. A system for monitoring an underground formation containing a fluid comprising:

least one measuring cell for placement in a cavity provided in the underground formation, an analyzer for placement on a ground surface of the underground formation, a sealed electrical connection for electrically connecting the at least one measuring cell to the analyzer, the at least one measuring cell including at least a first chamber, a second chamber which is impervious to entry of the fluid into the second chamber, and at least three sealed inner connectors which electrically connect the first chamber to the second chamber; and wherein the first chamber includes a plurality of orifices through which the fluid may pass into the first chamber from the formation, at least two inner electrodes electrically connected to at least two of the at least three sealed inner connectors, the sealed electrical connection being electrically connected to the inner connectors, and a fluid circulator electrically connected to the analyzer and to at least one of the connectors and to the sealed electrical connection and the first chamber is filled with a porous material having petrophysical and electrical properties.

2. A system as claimed in claim 1, comprising:

at least two outer electrodes, two inner connectors connecting the two chambers, two sealed outer connectors disposed on at least one wall of the first chamber, the wall being in contact with the formation, the outer electrodes cooperating with the two sealed outer connectors, the outer electrodes being electrically connected to the analyzer through the connection which is electrically connected to the two inner connectors and the two outer connectors.

3. A system as claimed in claim 1, wherein:

the sealed electrical connection includes an electrical power supply which supplies electrical power to the electrodes and the sealed electrical connection comprises a sealed sheath protecting at least the fluid circulator and the power supply.

4. A system as claimed in claim 2, wherein:

the sealed electrical connection includes an electrical power supply which supplies electrical power to the electrodes and the sealed electrical connection comprises a sealed sheath protecting at least the fluid circulator and the power supply.

5. A system as claimed in claim 1, wherein the petrophysical properties are at least porosity and permeability, and the electrical properties are at least electrical conductivity.

6. A system as claimed in claim 1, wherein the sealed electrical connection, the chambers and the connectors comprise PTFE.

7. A system as claimed in claim 2, wherein the sealed electrical connection, the chambers and the connectors comprise PTFE.

8. A system as claimed in claim 3, wherein the sealed electrical connection, the chambers and the connectors comprise PTFE.

9. A system as claimed in claim 4, wherein the sealed electrical connection, the chambers and the connectors comprise PTFE.

10. A system as claimed in claim 1, wherein the analyzer includes at least one of a fluid analyzer and a resistivity meter.

11. A system as claimed in claim 1, wherein the fluid circulator includes at least a pipe, a fluid suction system and a fluid reflux system.

12. A system as claimed in claim 1, wherein the fluid circulator includes at least two pipes, a fluid suction system and a fluid reflux system.

13. A system as claimed in claim 1, wherein the underground formation is geological storage site for a gas including $CO_2$ or methane.

14. A system as claimed in claim 11, wherein the system is calibrated prior to injecting gas into a geological storage site.

* * * * *